Figure 1:
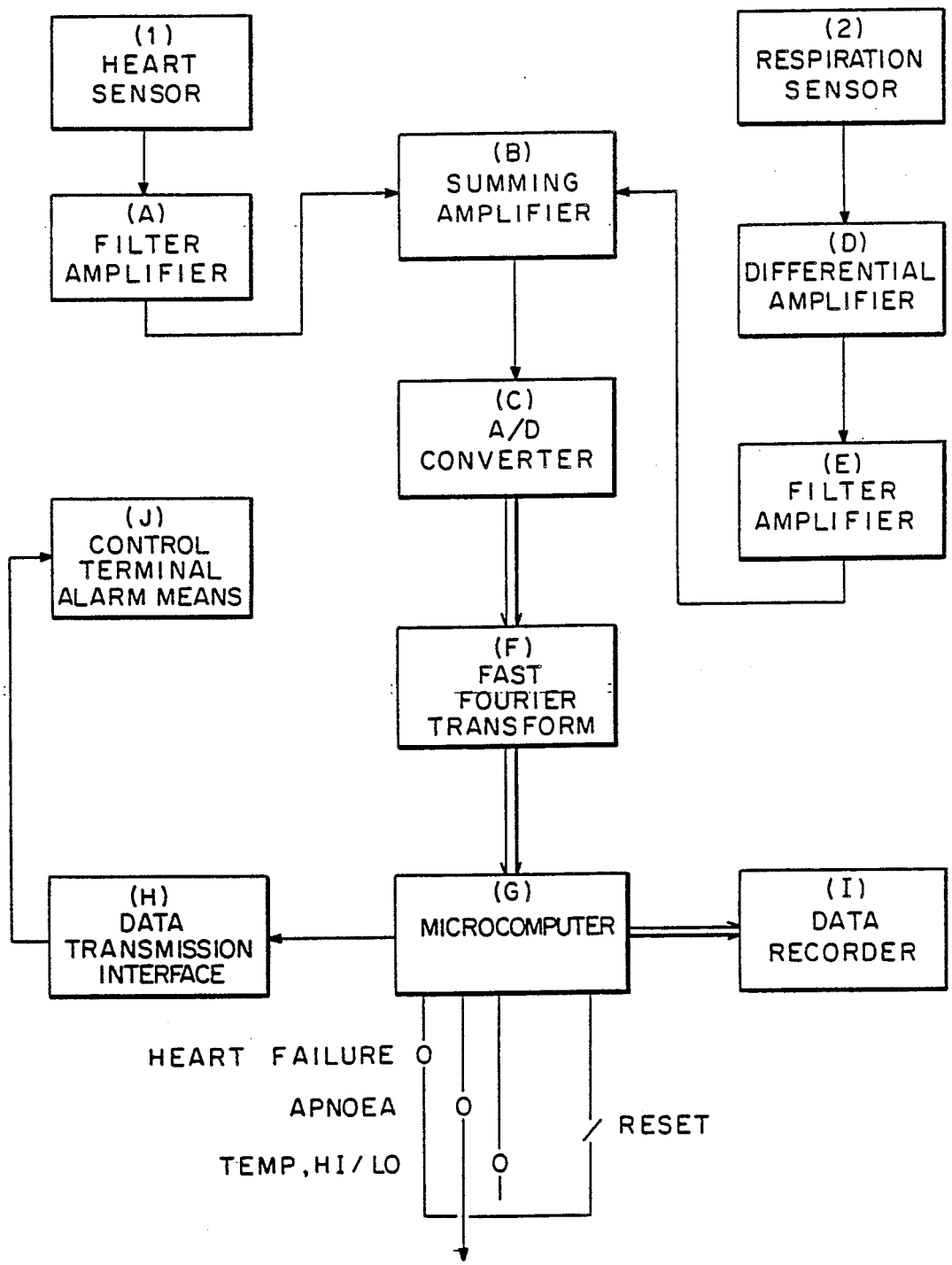

United States Patent [19]

Nedivi

[11] Patent Number: 5,002,060
[45] Date of Patent: Mar. 26, 1991

[54] MEDICAL MONITORING SYSTEM

[76] Inventor: Dror Nedivi, 41 Gordon Street, Petach Tikva, Israel

[21] Appl. No.: 366,373

[22] Filed: Jun. 14, 1989

[30] Foreign Application Priority Data

Jun. 16, 1988 [IL] Israel ........................... 86759

[51] Int. Cl.⁵ .............................................. A61B 5/02
[52] U.S. Cl. ...................................... 128/671; 128/715; 128/722; 310/329
[58] Field of Search ............... 128/670, 671, 700, 715, 128/716, 721, 722, 687, 689; 381/92, 94, 170, 174; 310/329

[56] References Cited

U.S. PATENT DOCUMENTS

| | | | |
|---|---|---|---|
| 3,325,799 | 6/1967 | Farris | 128/721 |
| 4,037,052 | 7/1977 | Doi | 381/170 |
| 4,066,072 | 1/1978 | Cummins | 128/706 |
| 4,146,885 | 3/1979 | Lawson, Jr. | 128/721 |
| 4,320,766 | 3/1982 | Alihanka et al. | 128/671 |
| 4,362,164 | 12/1982 | Little et al. | 128/715 |
| 4,422,458 | 12/1983 | Kravath | 128/671 |
| 4,425,921 | 1/1984 | Fujisaki et al. | 128/700 |
| 4,595,023 | 6/1986 | Bonnet | 128/721 |
| 4,608,994 | 9/1986 | Ozawa et al. | 128/670 |
| 4,790,326 | 12/1988 | Mather et al. | 128/689 |
| 4,884,578 | 12/1989 | Morgenstern | 128/670 |
| 4,889,130 | 12/1989 | Lee | 128/670 |
| 4,889,131 | 12/1989 | Salem et al. | 128/700 |

Primary Examiner—William E. Kamm
Assistant Examiner—Scott M. Getzow
Attorney, Agent, or Firm—Browdy and Neimark

[57] ABSTRACT

A monitoring system adapted simultaneously to monitor cardiac and respiratory, rates and characteristics and substantial changes in temperature of a living body. The system uses sensors which are passive and non-invasive, and remotely completely located off the living body. The system is adapted to distinguish the desired signals from the undesired environmental noise. Analog and microcomputer component process the signals in order to provide an alarm accompanied with displayed indication of any irregularities in the cardiac and respiratory, rates and characteristics; and substantial changes in temperature of the living body. The system also includes device to transmit said displayed data and alarm to a remote location as desired. An optional device to record said transmitted data is provided.

9 Claims, 2 Drawing Sheets

MEDICAL MONITORING SYSTEM

The present invention concerns a system for monitoring medical phenomena in order to detect changes in cardiac and respiratory rates and drastic changes in the body such as temperature.

DEFINITIONS (1) Medical Monitor—Device that detect and decode signals which are results of physiological situations.

(2) Invasive Monitor—Same as (1) which sensors must penetrate or at least make a direct contact with the body.

(3) Remote Passive Monitor—Same as (1) which sensors are remotely located off the body and do not transfer energy of any kind to the body.

(4) Domestic Monitor—Same as (1) which functions under domestic environment conditions and is simple to use.

* NOTE—We shall be using the above definitions either separately or combined.

Monitoring devices for persons potentially under stress due to either respiratory or cardiac disturbances, or body temperature changes are of utmost importance. Especially for new born babies where the danger of sudden infant death, or prolonged apneas exist.

Many such devices have been developed, most of them taking only the respiratory and cardiac changes into account. It is the purpose of this invention to design a system monitoring both the respiratory and cardiac changes as well as the body temperature changes deriving the information from changes in pulse rate.

Most of the monitoring equipments which exist today are Invasive. Some devices which are not invasive, have doubtful efficiency and reliability when in use;

The following are several types of invasive monitors which detect heart rate, which are known in the prior art.

(1) ECG MONITORS—require at least two electrodes to be attached to the body, as described in U.S. Pat. Nos. 4,630,614 and 4,269,195.

(2) ULTRASOUND—Must be attached to the chest.

(3) ACOUSTIC—Must be attached to the chest, or nostril as in U.S. Pat. Nos. 4,421,113 4,281,651.

(4) INFRARED—Which is attached to the finger. Nothing is known of the remote (detached) passive heart rate monitors.

(5) A sensor that detects air flow through the nostril. As in U.S. Pat. No. 4,036,217.

(6) A strap that is stretched across the chest to detect the chest movements during respiration. As in U.S. Pat. Nos. 3,802,419 and 4,540,002.

(7) A device attached to the matress U.S. Pat. No. 3,325,799. As in U.S. Pat. Nos. 4,146,885; 4,066,072; 3,631,438; and France PV No. 43858 No. 1,480,160;

(8) A CO2 sensor which is attached to the breathing system.

(9) A Thermistor sensor which is attached to the breathing system.

(10) Ultrasound or microwave doppler radar (invasive due to radiation). As in U.S. Pat. Nos. 3,875,929; 3,796,208.

(11) Inductance change respiratory electrodes. As in U.S. Pat. Nos. 3,911,899; 3,658,052.

The last five units refer to respiratory rate monitors, which effectiveness and reliability depends on the degree of invasivness.

There is also a sensor that detects mechanical movements of the chest. But this sensor, like the sensors No. (6) and (10) listed above are not reliable because they will not be able to distinguish between normal respiration and contraction of the chest during obstruction of the respiratory ways.

All the above mentioned devices prove to be impractical for long term overnight monitoring. The connection wires are strongly rejected. The conductive cream that must be used to coat the attached electrodes may have harmful effects. The above mentioned devices are thus most inconvenient and irritating, unreliable and some times even dangerous.

It is the object of the present invention, to provide a monitoring system which overcomes the above-mentioned drawbacks in that it is passive non-invasive, remote from the human body, and is adapted simultaneously to monitor both cardiac and respiratory rates as well as other body characteristics such as substantial changes in body temperature.

It is further the object of the present invention, to provide a monitoring system which is compact, easy to operate and comparatively inexpensive, so that it is practicable for general medical, as well as for domestic use.

The invention consists of a monitoring system adapted to detect and analyze both respiration and heart beat of an individual comprising of; sensor means adapted to detect respiration and heart beat, that are non-invasive, passive and remotely located off the body of the monitored individual; the said sensors feed the inputs of a filter amplifier to produce analog processed signals from the said respiration and heart vibrations; the said processed signals constitute the input of means to convert the said combined analog signal into digital form preferably analog to digital converter (A/D converter); the said digitized signal is applied to a digital Signal processor means; said processor means carry out analysis of the said digitized signals; said analysis result's filtered data that is a digital representation of the said vibrations produced by the heart beat and the respiration of the said monitored individual; the said processed data is further processed to produce an alarm upon irregularities in either the rate or characteristics of heart beat, or drastic change in body temperature that is derived from heart beat rate, or respiration indicating the cause of the alarm; the said system includes means to transmit the said alarm signal and the said indication display to any desired location; the said system has means to record and store the said data for future use.

In a preferred embodiment of the invention, the digital signal analysing is carried out by using the FFT (Fast Fourier Transform) method.

The invention can be illustrated as an example, in the accompanying drawings:

FIG. 1 illustrates the bloc diagram of the monitoring system.

Figure 2:
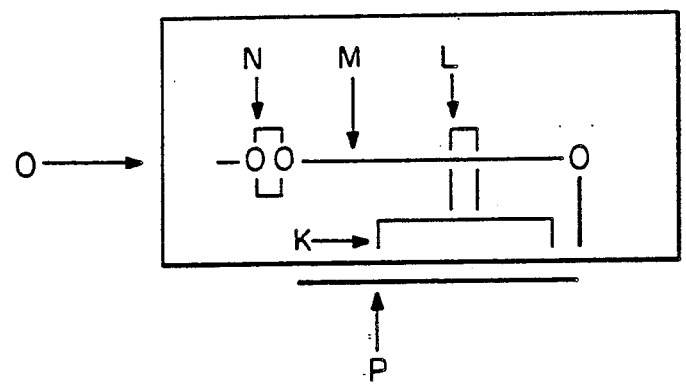
Figure 3:
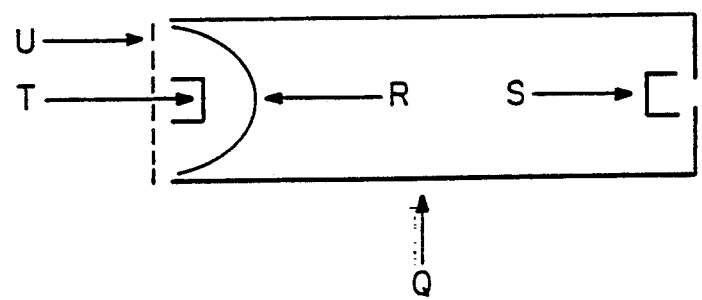

FIGS. 2 and 3 illustrate the two modified sensors. The monitoring system here illustrated, comprises two sensors. Sensor 1, which is destined to detect the cardiac pulse, is a piezoelectric element (K) in which the acoustic sensitive element consists of a mechanical arm (M) that is attached to a fixed point at one end, mechanically coupled (L) to the said piezoelectric element at it's middle, and has a small weight (N) mounted to it's other end, said arm is destined to have mechanical resonance of about 85 Hertz. The sensor is assembled into a small container (O) attached to the bed or mattress by some attachment means (P), (i.e. straps or double side stickybands, or velcro). Heart beat vibrations are being picked up by the relative motion of the container against the mechanical arm which tends to stay still due to it's moment of inertia.

The signals, picked up by sensor 1, are filtered and amplified by the filter amplifier (A) which has a gain of 50 db between 70 to 110 Hertz.

The second sensor 2, destined to detect the respiration, is a directional differential microphone which comprises of two capacitive microphones. One of these is directional (T), located at the focus of a parabolic reflector (R), and is intended to cover the area of the bed, while the other (S), is omnidirectional. The output signals from both microphones is applied to the differential amplifier (D) at which output there is a substantial gain, about 6 db of the signal which comes from the bed area, as against the background noise. This signal is passed to the filter amplifier (E) which has a gain of 40 db between 6000 to 7000 Hertz.

The signals from the filter amplifier (A) and that from the filter amplifier (E) are lead to the summing amplifier (B) (Adder). These signals are added therein and constitute the input of analog to the digital converter (A/d) (C). The signal from A/D (C) now has a digital form and is lead to the microprocessor (F). This microprocessor (F) is of the fast transform type preferably a FFT (Fast Fourier Transform) which analyzes digital signals. The data processed by FFT (F) is passed out to the microcomputer (G) which compares the existence of the two signals, i.e. cardiac pulse rate and respiration rate and characteristics, against data which was entered into the memory (internal RAM) of the microcomputer (G) by a preset operation, a process which can be carried out as desired.

Any discrepencies, exceeding the predetermined range, which has been fixed during the preset process, between the preset data and that coming from the FFT (F) will cause an alarm and will be displayed by the microcomputer (G). It will indicate the following phenomenon: (1) Apnea; (2) Cardiac failure; (3) High/Low temperature, derived from drastic changes in the cardiac rate, i.e. a higher cardiac pulse rate indicates a rise in body temperature; and (4) any other distortions in the function of respiration or heart beat of the monitored individual. The alarm signal and said displayed data from the microcomputer (G) are lead to the alarm and data transmission interface (H) which will transmit the said data and alarm either through wire or wireless channel to A control terminal (J) which can be located at any convenient location in the home, institution or the like. The control terminal (J) includes the alarm means, (i.e. buzzer, light, or other suitable means), it also includes a displaying means, (i.e. alphanumeric display, LEDs, or data terminal).

If desired, a data recorder and storage unit (I) may be included to record and store data taken from the microcomputer (G) for the purpose of viewing it when desired.

It can be appreciated from the above description, that by using the digital signal processing method in general, and the fast transform method in particular, the application of remote, i.e. non-invasive passive sensors for monitoring cardiac and respiratory rates and characteristic is made feasible. Thus, a medical monitoring system which is compact and inexpensive, using commercially available parts, can be obtained.

It is to be understood that many of the parts of the monitoring system above described may be replaced by other equivalent known parts without deviating from the scope of the present invention.

I claim:

1. A monitoring system adapted to detect and analyze both respiration and heart beat of an individual comprising:

sensor means adapted to detect respiration and heart beat signals, that are non-invasive, passive and remotely located off the body of the individual;

said sensor means connected to the inputs of filter amplifiers having inputs connected to said sensor means to produce analog processed signals from said respiration and heart beat signals;

said processed signals constitute the input to means for converting said analog signals into digital form with an analog to digital converter (A/D converter);

means for applying the resulting digitized signals to a digital signal processor means which carries out analysis of said digitized signals;

said analysis yields filtered data that is a digital representation of said heart beat and respiration signals produced by the heart beat and the respiration of said monitored individual;

means for further processing data to produce an alarm upon irregularities in either the rate or characteristics of the heart beat or respiration, or drastic change in body temperature that is derived from heart beat rate, and means for indicating the cause of the alarm;

said system including means to transmit the alarm signal and indication of the cause of the alarm to any desired location; and means to record and store data concerning said irregularities for future use.

2. A monitoring system as in claim 1, wherein said digital signal processing is carried out by fast transform methods, preferably FFT (Fast Fourier Transform);

said analyzed data is applied to a microcomputer, that performs further processing of said analyzed data, and compares characteristics of said signals from the individual, against data, concerning the same characteristics, that were recorded from said individual prior to monitoring, processed and internally stored by said system in preset operation;

said preset operation can be carried out so that any changes exceeding a predetermined range which has been fixed at an earlier time, preferably during the preset operation, between a continuous data flow and preset data internally stored during said preset operation, will cause an alarm accompanied by a displayed indication of said change that caused the alarm.

3. A monitoring system as in claim 1 wherein said sensor means to detect heart beat signals, is adapted to pick up the vibrations produced by the heart beat of the monitored individual within the frequency range of 60 to 120 Hertz, and is adapted to be attached to a bed or a mattress on which said monitored individual lies.

4. A monitoring system as in claim 1 wherein said sensor means for detecting heart beat signals is a piezoelectric acoustic pick up, in which an acoustic sensitive element comprises a mechanical arm that is attached to a fixed point at one end, is mechanically coupled to a piezoelectric element at it's middle and has a small weight mounted to it's other end;

said arm having a mechanical resonance of about 85 Hertz;

wherein said sensor means is assembled into a small container attached to a bed or a mattress;

and wherein heart beat vibrations are picked up by the relative motion of said container against the mechanical arm which tends to stay still due to its moment of inertia.

5. A monitoring system as in claim 1 wherein said sensor means to detect respiration is a directional microphone.

6. A monitoring system as in claim 5 wherein said sensor means to detect respiration is a directional microphone consisting of two capactive microphones; one is mounted at the focus of a parabolic reflector so that it will pick up respiration vibration signals from one direction only, while the other is mounted at the back of the reflector and has omni-directional characteristics for picking up background noise.

7. A monitoring system as in claim 1 wherein the signals from each of said sensor means are each lead to said filter amplifiers whose outputs are lead to a summing amplifier the output of which constitutes the input of an analog to digital converter.

8. A monitoring system as in claim 1 having a differential amplifier that is utilized to differentiate between the signals picked up from the individual and the background noise.

9. A monitoring system as in claim 2 wherein said microcomputer:
  is adapted to provide a continuous reading of processed heart beat and respiration signals, and comprises means to transmit said reading and said alarm signal and an indication of the cause of the alarm, to a desired location; and
  means to record and store said reading.

* * * * *